United States Patent
Komukai

(10) Patent No.: US 9,046,693 B2
(45) Date of Patent: Jun. 2, 2015

(54) ILLUMINATION OPTICAL SYSTEM UNIT FOR ENDOSCOPE AND METHOD OF MANUFACTURING THE SAME

(71) Applicant: FUJIFILM Corporation, Tokyo (JP)

(72) Inventor: Makito Komukai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/273,610

(22) Filed: May 9, 2014

(65) Prior Publication Data

US 2014/0340926 A1 Nov. 20, 2014

Related U.S. Application Data

(63) Continuation of application No. PCT/JP2012/077529, filed on Oct. 25, 2012.

(30) Foreign Application Priority Data

Nov. 10, 2011 (JP) ................................. 2011-246518

(51) Int. Cl.
*B32B 37/00* (2006.01)
*G02B 23/24* (2006.01)
*A61B 1/00* (2006.01)
*F21V 8/00* (2006.01)
*A61B 1/06* (2006.01)

(52) U.S. Cl.
CPC .......... *G02B 23/2476* (2013.01); *A61B 1/0011* (2013.01); *G02B 23/2469* (2013.01); *B32B 37/00* (2013.01); *B32B 2535/00* (2013.01); *B32B 2551/00* (2013.01); *G02B 6/0008* (2013.01); *A61B 1/00096* (2013.01); *A61B 1/0653* (2013.01)

(58) Field of Classification Search
None
See application file for complete search history.

(56) References Cited

U.S. PATENT DOCUMENTS

2002/0177751 A1* 11/2002 Ueno et al. .................... 600/160
2008/0039695 A1* 2/2008 Takaoka et al. ............... 600/178
2008/0112182 A1* 5/2008 Kazakevich .................. 362/551

FOREIGN PATENT DOCUMENTS

| EP | 0 454 325 A2 | 10/1991 |
| JP | 5-281454 A | 10/1993 |
| JP | 2006-26135 A | 2/2006 |

(Continued)

OTHER PUBLICATIONS

International Search Report issued in PCT/JP2012/077529, mailed on Nov. 20, 2012.

(Continued)

*Primary Examiner* — Britt D Hanley
(74) *Attorney, Agent, or Firm* — Birch, Stewart, Kolasch & Birch, LLP

(57) ABSTRACT

An illumination optical system unit 26A includes an optical fiber 39A, a fluorescent body 40, a ferrule 60 as a holding member that holds the fluorescent, body 40 and the optical fiber 39A, a cylindrical first sleeve member 61 that covers the outer periphery of the fluorescent body 40, and a protective cover 38 that seals the tip side of the fluorescent body 40. The ferrule 60 holds the optical fiber 39A and the fluorescent body 40, and is inserted into the first sleeve member 61. A magnetic metal film 67 is provided on the surface of a fluorescent body-holding portion 69 of the ferrule 60. The tip of the protective cover 38 and a magnet 75 are allowed to come into contact wife each other to generate magnetic force between those two, so that the fluorescent body 40 comes into close contact with the protective cover 38.

19 Claims, 12 Drawing Sheets

(56) References Cited

FOREIGN PATENT DOCUMENTS

| | | |
|---|---|---|
| JP | 2007-20937 A | 2/2007 |
| JP | 2011-72424 | 4/2011 |
| JP | 2011-167442 A | 9/2011 |

OTHER PUBLICATIONS

PCT/ISA/237—Issued in PCT/JP2012/077529, mailed on Nov. 20, 2012.

* cited by examiner

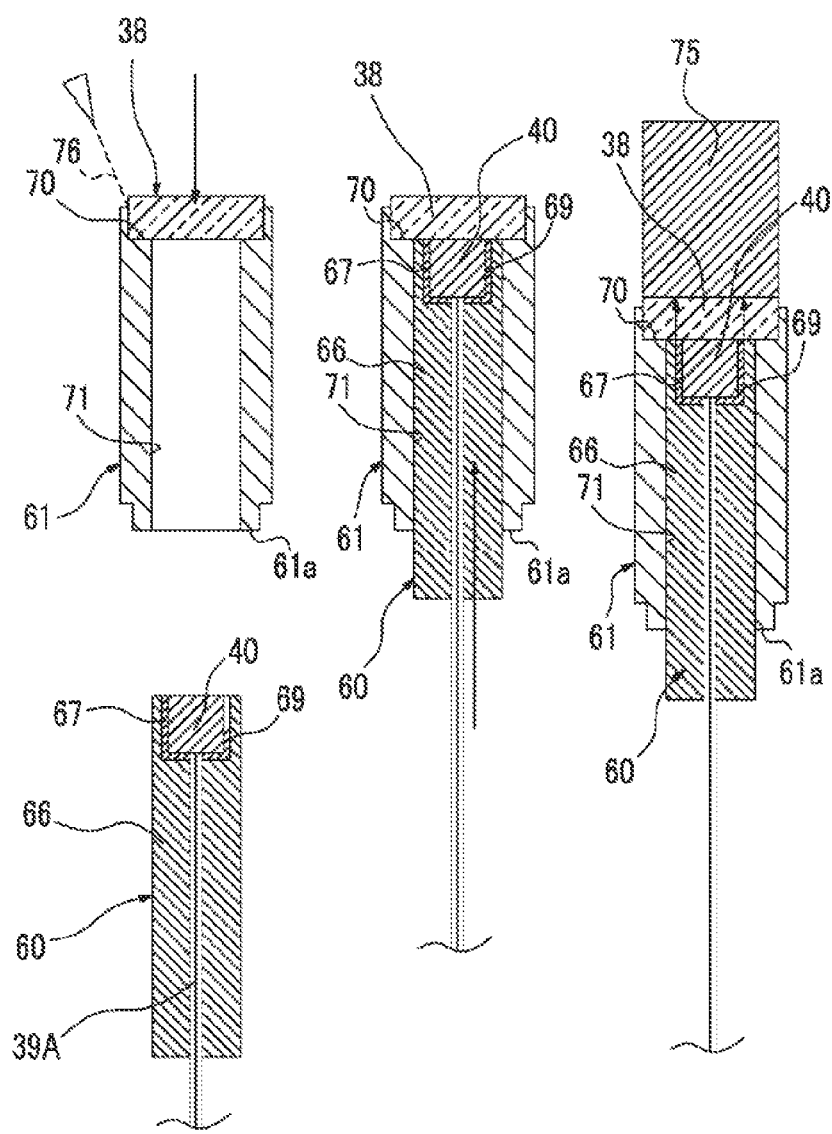

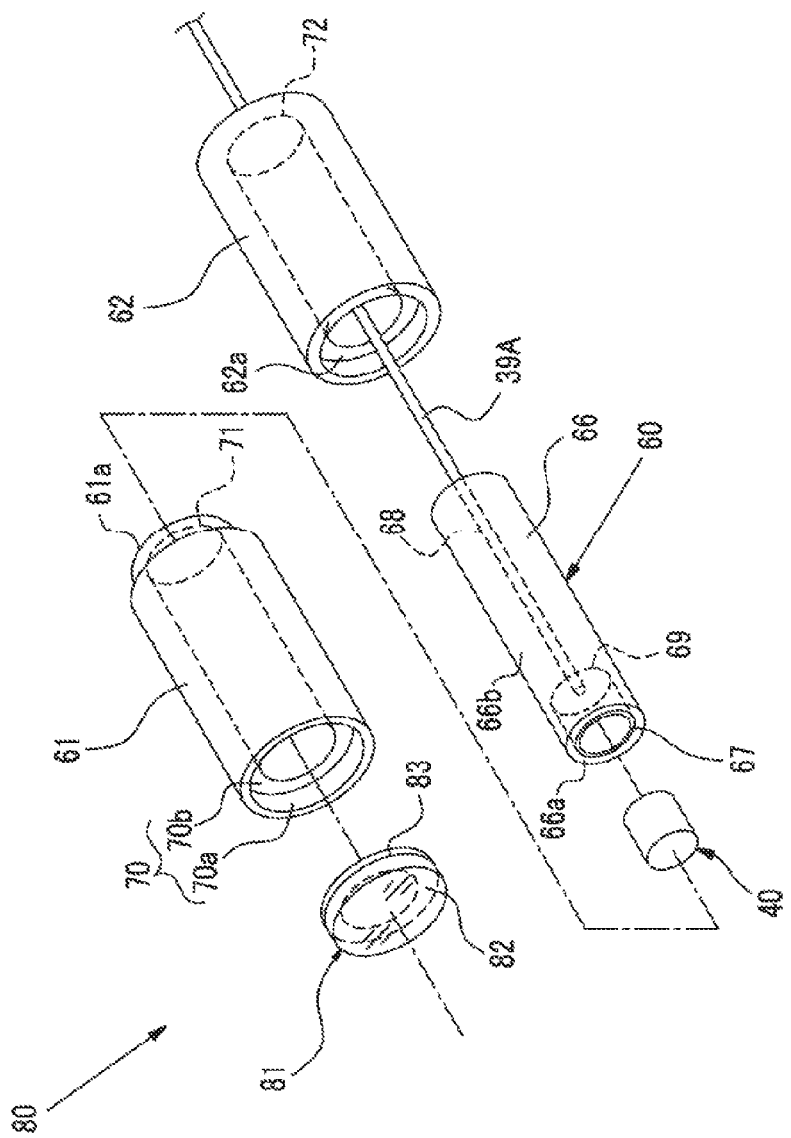

FIG. 9A
FIG. 9B
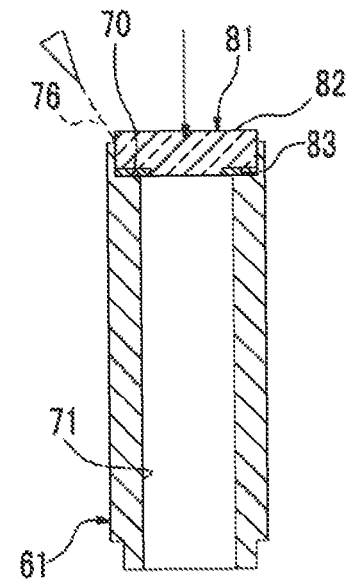
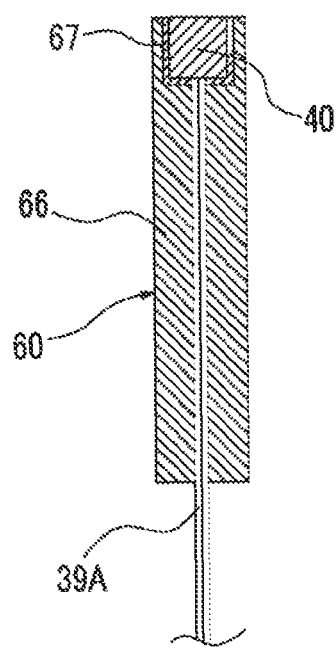
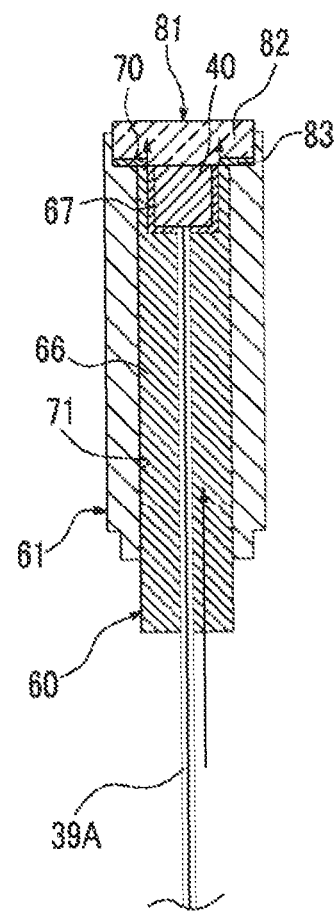

ILLUMINATION OPTICAL SYSTEM UNIT FOR ENDOSCOPE AND METHOD OF MANUFACTURING THE SAME

CROSS REFERENCE TO RELATED APPLICATIONS

This application is a Continuation of PCT International Application No. PCT/JP2012/077529 filed on Oct. 25, 2012, which claims priority under 35 U.S.C §119(a) to Patent Application No. 2011-246518 filed in Japan on Nov. 10, 2011, all of which are hereby expressly incorporated by reference into the present application.

BACKGROUND OF THE INVENTION

1. Field of the Invention

The present invention relates to an illumination optical system unit for an endoscope that irradiates a portion to be observed inside a subject with illumination light to observe inside the subject, and a method of manufacturing the illumination optical system unit for an endoscope.

2. Description of the Related Art

In the past, diagnosis using an endoscope has been widely used in a medical field. An endoscope includes an observation window which is formed at a tip of an insertion section to be inserted into a subject and through which image light of the subject is taken, and an illumination window through which illumination light is emitted to the subject. The endoscope is connected to a light source device through a cord or a connector. The light source device includes a light source for supplying illumination light for the illumination inside the subject to the endoscope. The illumination light supplied from the light source is guided to the tip of an insertion section through an optical fiber that is inserted into the endoscope.

A white light source, such as a xenon lamp or a halogen lamp, could have been used as the light source of the light source device. A ratio of a space, which is occupied by the white light source and peripheral components of the white light source, to an inner space is high in a light source device using the white light source, which makes it difficult to reduce the size of the light source device. For this reason, a light source device using a laser light source instead of the white light source has been used in recent years. JP2007-20937A and JP2011-72424A disclose an endoscope that irradiates inside a body cavity with white illumination light by guiding laser light, which is supplied from the light source device using the laser light source, to a tip of the insertion section through an optical fiber and exciting a fluorescent body, which is disposed at a tip of the optical fiber, by the laser light to allow the fluorescent body to emit light.

Further, the endoscope needs to emit illumination light having higher intensity. For this reason, a reflective film having high reflectance is provided around the fluorescent body to efficiently use the light or the like, which is excited and emitted, as illumination light. It is known that a metal film made of silver, aluminum, or the like is suitable as the reflective film having high reflectance.

However, in diagnosis using an endoscope, moisture level is high in the insertion section of the endoscope inserted into the body cavity and grease containing molybdenum disulfide is applied to movable components and the like, which are used to bend the insertion section, as a lubricant. Further, the endoscope is subjected to washing and disinfection process, in which the endoscope is immersed in disinfectant containing peracetic acid and the like, after diagnosis. Since water or grease and chemicals, such disinfectant, easily enter the insertion section of the endoscope as described above, the degradation of the fluorescent body or the reflective film easily affected by water or chemicals may easily occur.

Further, a projection unit (an illumination optical system unit for an endoscope) disclosed in JP2011-72424A includes an outer cylindrical member as a sleeve member that covers the outer periphery of the fluorescent body, sapphire glass as a protective cover that covers the tip side of the fluorescent body, and a ferrule as a holding member that holds an optical fiber and is disposed at the base end side of the fluorescent body. The base end side of the outer cylindrical member is sealed while the optical fiber extends, and the tip side of the outer cylindrical member is sealed while adhering to the sapphire glass.

SUMMARY OF THE INVENTION

However, the fluorescent body and the protective cover do not close contact with each other and a gap is formed in the illumination optical system unit disclosed in JP2011-72424A. Further, since chemicals or water cause the degradation of the fluorescent body or the reflective film if entering the gap formed between the protective cover and the fluorescent body, a structure for sealing the fluorescent body is not sufficient. Further, considering a manufacturing step of sealing the fluorescent body while removing a gap between the fluorescent body and the protective cover in the illumination optical system unit disclosed in JP2011-72424A, the base end side of the sleeve member and the holding member should be adhered to each other while the holding member is pushed into the sleeve member and toward the protective cover so as to come into close contact with the fluorescent body and the protective cover after the protective cover adheres to sleeve member. However, there is a possibility that the optical fiber held by the holding member may be damaged when the holding member is pushed toward the protective cover. When the optical fiber is damaged, the yield rate of the illumination optical system unit is lowered.

The invention has been made in consideration of the problems, and an object of the invention is to prevent the degradation of a fluorescent body by reliably sealing a tip side of the fluorescent body with a simple structure.

An illumination optical system unit for an endoscope of the invention includes: an optical fiber that guides laser light supplied from a laser light source to a tip thereof and emits the laser light; a fluorescent body that is excited by the laser light emitted from the optical fiber and emits fluorescent light and forms white light formed of the fluorescent light and the laser light; a holding member including a fluorescent body-holding portion of which a tip side is opened and which holds the fluorescent body and a through hole which continues to a base end of the fluorescent body-holding portion and into which the optical fiber is inserted, at least a part of the holding member being formed of a magnetic body; a sleeve member of which a tip and a base end are opened and into which the holding member is fitted, the optical fiber protruding from the base end of the sleeve member; a protective cover that covers a tip side of the fluorescent body and allows the fluorescent light and the laser light to be transmitted therethrough; a first sealing portion that is formed by the adhesion between the protective cover and the sleeve member and seals the tip side of the fluorescent body; and a second sealing portion that allows the holding member and the sleeve member to adhere to each other so that a tip of the holding member is allowed to come into close contact with the protective cover by biasing the holding member toward the protective cover by magnetic force after the protective cover and the sleeve member adhered to each other, and seals a base end side of the fluorescent body.

It is preferable that the second sealing portion be formed so that a magnet is disposed on the protective cover to bias the holding member toward the protective cover by magnetic force.

It is preferable that a part of the protective cover be made of a magnet and the second sealing portion be formed so that the holding member is biased toward the protective cover by magnetic force generated between the protective cover and the holding member.

The illumination optical system unit for an endoscope may further includes a fitting member that is fitted to the protective cover and is made of a magnet, and it is preferable that the second sealing portion be formed so that the holding member is biased toward the protective cover by magnetic force generated between the fitting member and the holding member. Further, it is preferable that the fitting member be a fixing member that is fitted to the sleeve member together with the protective cover and fixes the protective cover to the sleeve member.

It is preferable that the first sealing portion be made of an adhesive containing a magnetic body and the second sealing portion be formed so that the holding member is biased toward the protective cover by magnetic force generated between the adhesive and the holding member.

It is preferable that the holding member includes a body that is formed of a non-magnetic body, and a metal film that is provided on the surface of the fluorescent body-holding portion, is made of magnetic metal, and reflects white light emitted from the fluorescent body.

It is preferable that the holding member includes a body that is made of a magnet, and a metal film that is provided on the surface of the fluorescent body-holding portion, is made of non-magnetic metal, and reflects white light emitted from the fluorescent body.

It is preferable that the holding member includes a body that is formed of a non-magnetic body and a magnet that is provided at a base end side of the body.

An illumination optical system unit includes an optical fiber that guides laser light supplied from a laser light source to a tip thereof and emits the laser light, a fluorescent body that is excited by the laser light emitted from the optical fiber and emits fluorescent light and forms white light formed of the fluorescent light and the laser light, a holding member including a fluorescent body-holding portion of which a tip side is opened and which holds the fluorescent body and a through hole which continues to a base end of the fluorescent body-holding portion and into which the optical fiber is inserted, a sleeve member into which the holding member is fitted and of which a tip and a base end are opened, and a protective cover that covers a tip side of the fluorescent body and allows the fluorescent light and the laser light to be transmitted therethrough. A method of manufacturing the illumination optical system unit for an endoscope of the invention includes: a first sealing step of sealing the tip side of the fluorescent body by allowing the sleeve member and the protective cover to adhere to each other; and a second sealing step of sealing a base end side of the fluorescent body by allowing the sleeve member and the holding member to adhere to each other so that a tip of the holding member is allowed to come into close contact with the protective cover by inserting the holding member into the sleeve member, allowing the optical fiber to protrude from base ends of the holding member and the sleeve member, and biasing the holding member toward the protective cover by magnetic force after the sleeve member and the protective cover adhere to each other.

According to the invention, the protective cover and the sleeve member adhered to each other and the holding member is biased toward the protective cover by magnetic force. Accordingly, since the sleeve member and the holding member adhere to each other while the holding member tip comes into close contact with the protective cover, it is possible to prevent the degradation of the fluorescent body by reliably sealing the fluorescent body with a simple structure. Further, since the fluorescent body and the protective cover are allowed to come into close contact with each other by magnetic force-biasing, it is not necessary to push the optical fiber and it is possible to improve a yield rate.

BRIEF DESCRIPTION OF THE DRAWINGS

FIGS. 7A to 7C are explanation views illustrating first and second sealing steps.

FIG. 8 is an exploded perspective view showing the structure of a second embodiment.

FIG. 9A and FIG. 9B are explanation views illustrating first and second sealing steps of the second embodiment.

DESCRIPTION OF THE PREFERRED EMBODIMENTS

Figure 1:
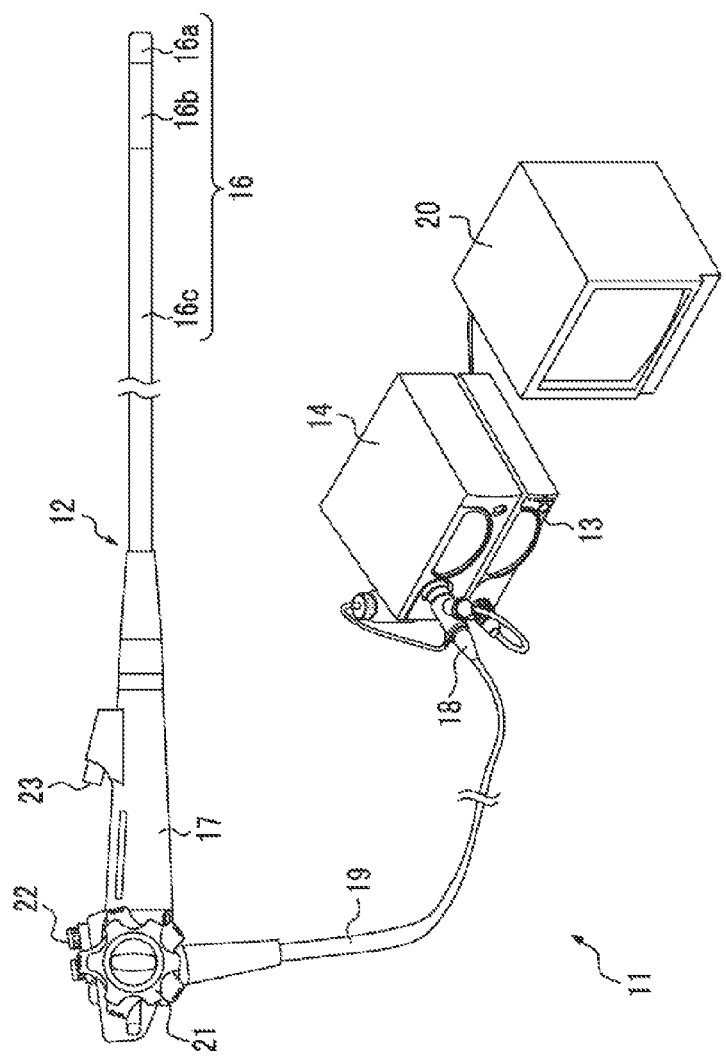
FIG. 1 is an external view showing the structure of an electronic endoscope system.

As shown in FIG. 1, an electronic endoscope system 11 includes an electronic endoscope 12, a processor device 13, and a light source device 14. The electronic endoscope 12 includes a flexible insertion section 16 that is inserted into the body of a subject, an operation section 17 that is connected to a base end portion of the insertion section 16, a connector 18 that is connected to the processor device 13 and the light source device 14, and a universal cord 19 that connects the operation section 17 to the connector 18.

Figure 4:
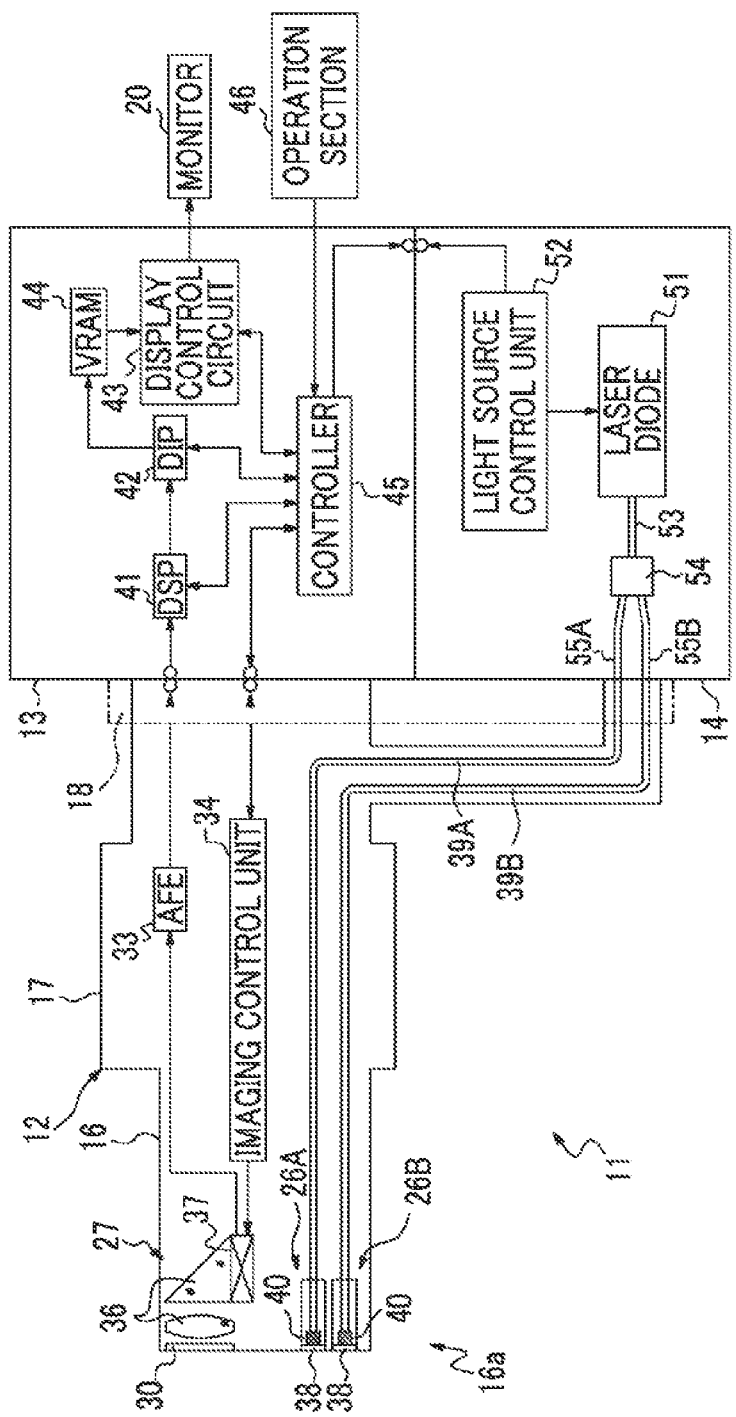
FIG. 4 is a block diagram showing the electrical configuration of the electronic endoscope system.

The insertion section 16 includes a tip portion 16a which is provided at the tip of the insertion section and in which a CCD type image sensor (see FIG. 4. Hereinafter, referred to as a CCD) 37 for taking an image inside a subject is built, a bendable portion 16b that is connected to a base end of the tip portion 16a, and a flexible tube portion 16c that is connected to a base end of the bendable portion 16b.

The operation section 17 is provided with operation members that are as an angle knob 21 for allowing the bendable portion 16b to be bent vertically and laterally and an air supply/water supply button 22 for allowing air or water to be ejected from the tip portion 16a. Further, the operation section 17 is provided with a forceps port 23 that allows a treatment tool, such as an electric scalpel, to be inserted into a forceps channel (not shown).

The processor device 13 is electrically connected to the light source device 14, and generally controls the operation of the electronic endoscope system 11. The processor device 13 controls the drive of the CCD 37 by supplying power to the electronic endoscope 12 through the universal cord 19 and a transmission cable that is inserted into the insertion section 16. Further, the processor device 13 acquires an imaging signal that is output from the CCD 37 through the transmission cable, and generates image data by performing various kinds of image processing. The image data, which are generated by the processor device 13, are displayed on a monitor 20, which is connected to the processor device 13 through a cable, as observed images.

Figure 2:
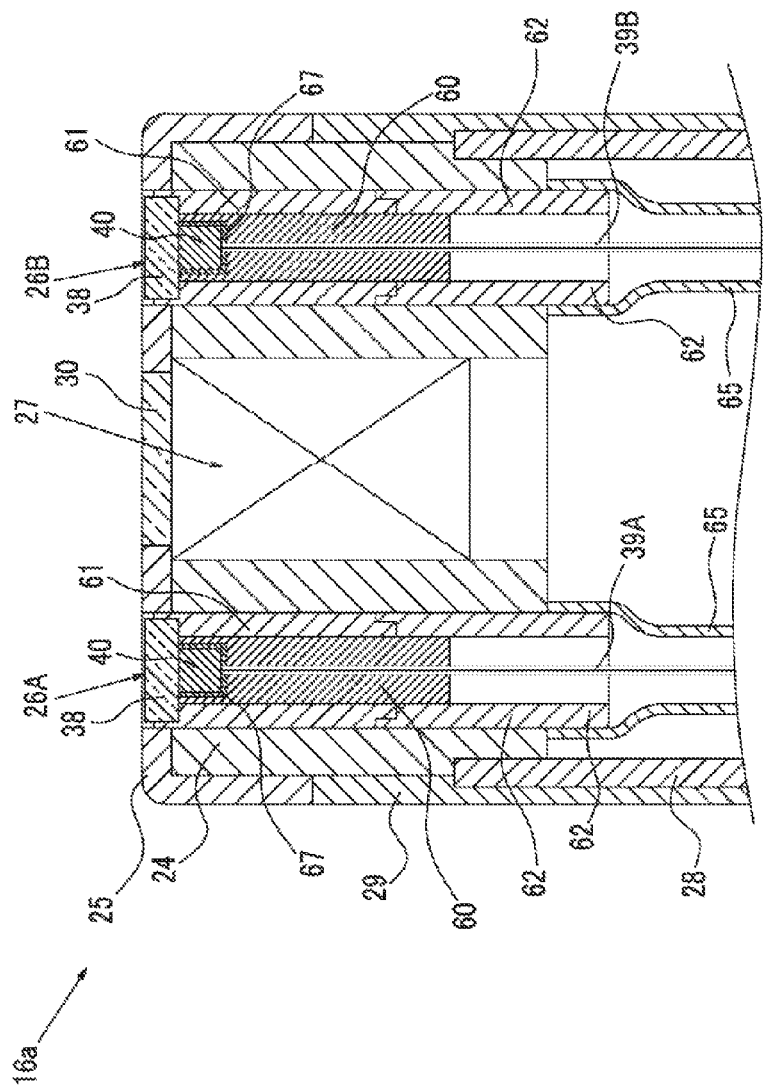
FIG. 2 is a cross-sectional view of a main portion showing the structure of a tip portion of an electronic endoscope.

As shown in FIG. 2, the tip portion 16a includes a tip hard portion 24 and a tip-protection cap 25 that is mounted on the tip of the tip hard portion 24. The tip hard portion 24 is made of metal such as stainless steel, and a plurality of through holes are formed at the tip hard portion 24 along a longitudinal direction. Various components, such as illumination optical system units 26A and 26B, an imaging unit 27, a forceps channel, and an air supply/water supply channel (not shown), are mounted in the respective through holes of the tip hard portion 24. A rear end of the tip hard portion 24 is connected to a bendable piece 28 of a tip that forms the bendable portion 16b. Further, the outer periphery of the tip hard portion 24 is covered with an outer tube 29.

Figure 3:
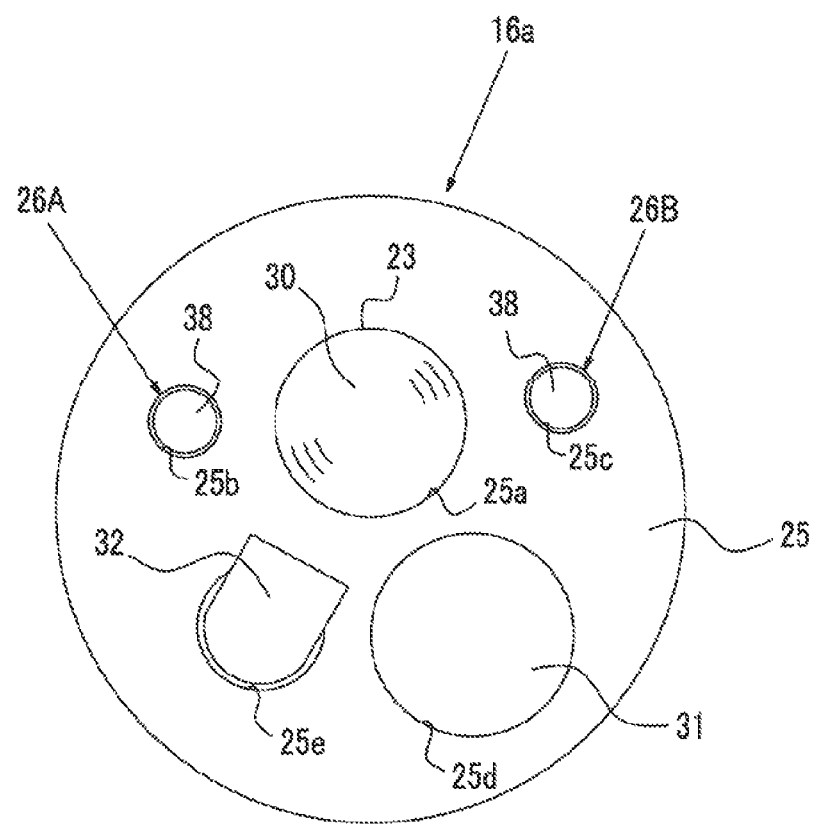
FIG. 3 is a plan view of the tip portion of the electronic endoscope.

The tip-protection cap 25 is made of rubber, a resin, or the like, and through holes are formed in the tip-protection cap 25 at positions corresponding to various components that are held by the tip hard portion 24. As shown in FIG. 3, an observation window 30, the illumination optical system units 26A and 26B, a forceps outlet 31, an air supply/water supply nozzle 32, and the like are exposed to the outside of through holes 25a to 25e of the tip-protection cap 25. The pair of illumination optical system units 26A and 26B are disposed at positions that are symmetrical to each other with the observation window 30 interposed therebetween.

As shown in FIG. 4, the electronic endoscope 12 includes the imaging unit 27 and the illumination optical system units 26A and 26B that are provided at the tip portion 16a, and an AFE (analog signal processing circuit) 33 and an imaging control unit 34 that are provided at the operation section 17.

The imaging unit 27 is disposed in the observation window 30, and includes an imaging optical system 36 that is formed of a lens group and a prism and the CCD 37 in which an image inside the subject is formed on an imaging plane by the imaging optical system 36. The CCD 37 accumulates signal charges by photoelectrically converting the image inside the subject, which is formed on the imaging plane, and outputs the accumulated signal charges as imaging signals. The output imaging signals are sent to the AFE 33. The AFE 33 includes a correlated double sampling (CDS) circuit, an automatic gain control (AGC) circuit, an A/D converter, and the like (of which all are not shown). The CDS performs correlated double sampling processing on the imaging signals that are output from the CCD 37, and removes noises that are generated by the drive of the CCD 37. The AGC amplifies the imaging signals from which noises have been removed by the CDS.

When the electronic endoscope 12 and the processor device 13 are connected to each other, the imaging control unit 34 is connected to a controller 45 provided in the processor device 13. When receiving an instruction from the controller 45, the imaging control unit 34 sends a drive signal to the CCD 37. The CCD 37 outputs imaging signals to the AFE 33 at a predetermined frame rate on the basis of the drive signal that is sent from the imaging control unit 34.

The illumination optical system units 26A and 26B are units that irradiate inside the subject with illumination light. Tip portions of the illumination optical system units 26A and 26B are sealed by protective covers 38, and are exposed to the outside through the end face of the tip portion 16a, that is, through holes 25b and 25c of the tip-protection cap 25 as illumination windows.

Optical fibers 39A and 39B, which form the illumination optical system units 26A and 26B, guide blue laser light, which is supplied from the light source device 14, and emit the blue laser light to fluorescent bodies 40 that are provided on emission end sides thereof. Hereinafter, the emission end sides of the optical fibers 39A and 39B are referred to as "tip sides", and incident end sides of the optical fibers 39A and 39B are referred to as "base end sides". The fluorescent bodies 40 absorb a part of the blue laser light emitted from the optical fibers 39A and 39B, and excite and emit green to yellow light. For this reason, blue light, which is transmitted through the fluorescent bodies 40 while being diffused in the fluorescent bodies 40, and green to yellow fluorescent light, which is excited and emitted from the fluorescent bodies 40, are mixed to each other in the illumination optical system units 26A and 26B, so that white (pseudo white) illumination light is formed. The irradiation range of the illumination light is substantially equal to or larger than the range of an image that is taken by the electronic endoscope 12, and the entire observed image is substantially uniformly irradiated with the illumination light.

The processor device 13 includes a digital signal processing circuit (DSP) 41, a digital image processing circuit (DIP) 42, a display control circuit 43, a VRAM 44, the controller 45, an operation section 46, and the like.

The controller 45 generally controls the operation of the entire processor device 13. The DSP 41 generates image data by performing various kinds of signal processing, such as color separation, color interpolation, gain correction, white balance adjustment, and gamma correction, on the imaging signals that are output from the AFE 33 of the electronic endoscope 12. The image data, which are generated by the DSP 41, are input to a working memory of the DIP 42. Further, the DSP 41 generates data for ALC control, which are required for the automatic light control (ALC control) of the amount of illumination light, such as an average luminance value that is an average of luminance values of the respective pixels of the generated image data, and inputs the data for ALC control to the controller 45.

The DIP 42 performs various kinds of image processing, such as electronic variable magnification, color enhancement processing, and edge enhancement processing, on the image data that are generated by the DSP 41. The image data, which has been subjected to the various kinds of image processing performed by the DIP 42, are temporarily stored in the VRAM 44 as observed images, and are then input to the display control circuit 43. The display control circuit 43 selects and acquires an observed image from the VRAM 44, and displays the observed image on the monitor 20.

The operation section 46 is formed of well-known input devices, such as an operation panel, a mouse, and a keyboard, which are provided in a housing of the processor device 13. The controller 45 operates the respective sections of the electronic endoscope system 11 according to an operation signal that is sent from the operation section 46 or the operation section 17 of the electronic endoscope 12.

The light source device 14 includes a laser diode (LD) 51 as a laser light source and a light source control unit 52. The LD 51 is a light source that emits blue laser light having a center wavelength of 445 nm, and the blue laser light is guided to an optical fiber 53 through a condensing lens (not shown) and the like. The optical fiber 53 is connected to two optical fibers 55A and 55B through a branch coupler 54. The optical fibers 55A and 55B are connected to the optical fibers 39A and 39B of the electronic endoscope 12 through a connector 18. For this reason, blue laser light emitted from the LD 51 enters the fluorescent bodies 40 that form the illumination optical system units 26A and 26B. Further, when the blue laser light enters the fluorescent bodies, the blue laser light is mixed to the green to yellow fluorescent light, which is excited and emitted from the fluorescent bodies 40, and inside the subject is irradiated with the mixed light as white (pseudo white) illumination light.

The light source control unit 52 adjusts the turn-on/turn-off timing of the LD 51 according to an adjustment signal or a synchronous signal that is input from the controller 45 of the processor device 13. Further, the light source control unit 52 adjusts the amount of illumination light, which irradiates inside the subject, by communicating with the controller 45 and adjusting the amount of light generated from the LD 51. The control of the amount of illumination light, which is performed by the light source control unit 52, is ALC (automatic light control) control that automatically adjusts the amount of illumination light according to the brightness or the like of the observed image having been taken, and performed on the basis of the data for ALC control that are generated by the DSP 41.

Figure 5:
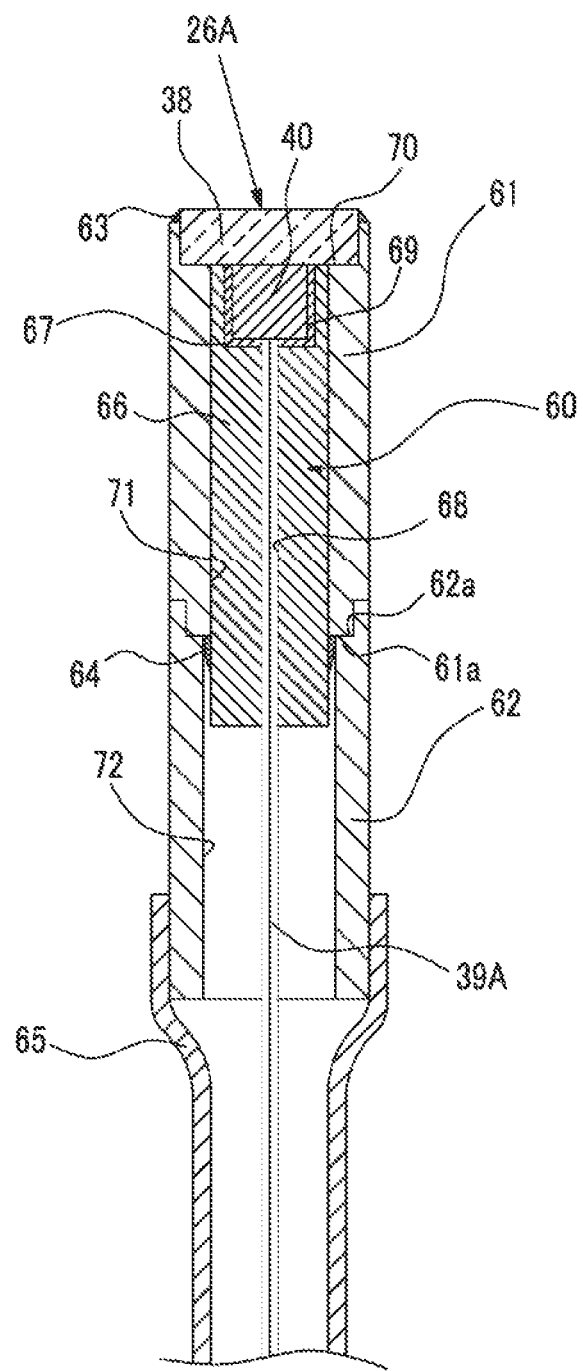
FIG. 5 is a cross-sectional view showing the structure of an illumination optical system unit.
Figure 6:
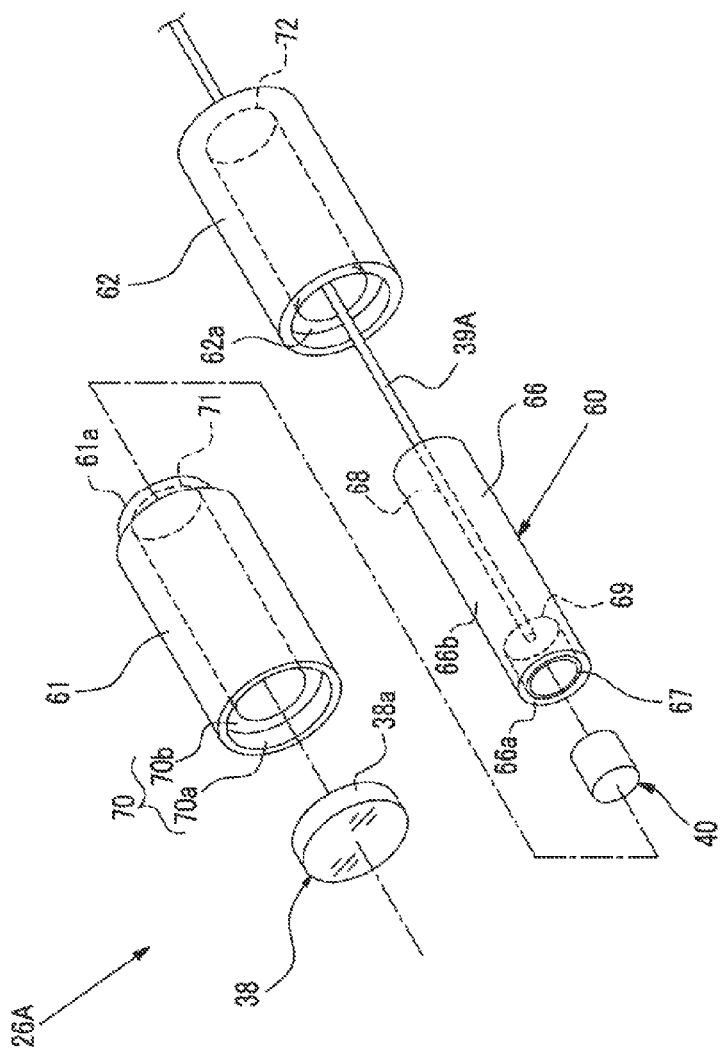
FIG. 6 is an exploded perspective view showing the structure of the illumination optical system unit.

As shown in FIGS. 5 and 6, the illumination optical system unit 26A includes the optical fiber 39A of a single mode, the fluorescent body 40, a ferrule 60 as a holding member that holds the fluorescent body 40 and the optical fiber 39A, first and second cylindrical sleeve members 61 and 62 that cover the outer periphery of the fluorescent body 40, the protective cover 38 that covers the tip side of the fluorescent body 40, a first sealing portion 63 that seals the tip side of the fluorescent body 40, and a second sealing portion 64 that seals the base end side of the fluorescent body 40. Further, the illumination optical system unit 26B includes the optical fiber 39B, the fluorescent body 40, a ferrule 60, sleeve members 61 and 62, the protective cover 38, and first and second sealing portions 63 and 64. As in the illumination optical system unit 26A, the ferrule 60 holds the fluorescent body 40 and the optical fiber 39B, the sleeve members 61 and 62 cover the outer periphery of the fluorescent body 40, the protective cover 38 covers the tip of the fluorescent body, and the sealing portions 63 and 64 that seal the tip and the base end side of the fluorescent body 40, respectively. Furthermore, the outer peripheral surfaces of the optical fibers 39A and 39B are covered with protective tubes 65. The tip portion of the protective tube 65 is fixed to the outer peripheral surface of the second sleeve member 62.

The ferrule 60 includes a ferrule body 66, and a metal film 67 that is made of magnetic metal. The ferrule body 66 is formed in a substantially cylindrical shape, and includes an insertion hole 68 into which the optical fiber 39A is inserted. A fluorescent body-holding portion 69, which holds the fluorescent body 40, is formed at the tip portion of the ferrule body 66. The fluorescent body-holding portion 69 is formed in the shape of a recess which is recessed from an end face 66a of the ferrule body 66 so as to correspond to the outer shape of the fluorescent body 40 and of which the tip side facing the protective cover 38 is opened. The insertion hole 68 continues to the base end of the fluorescent body-holding portion 69.

A metal film 67 is formed on the surface of the fluorescent body-holding portion 69. The metal film 67 is a magnetic body and functions as a reflective film. The metal film 67 is formed made of magnetic metal, for example, nickel, and is formed in the shape of a thin film by plating, deposition, spattering, or the like. Meanwhile, the ferrule body 66 is made of a non-magnetic material, for example, metal, such as SUS, or ceramic.

The fluorescent body 40 is formed so as to contain a fluorescent material that is excited by blue laser light and emits green to yellow fluorescent light, for example, YAG or BAM (BaMgAl10O17) in a base material, such as inorganic glass. The fluorescent body 40 is held in the fluorescent body-holding portion 69 while coming into contact with the metal film 67. Illumination light, which is emitted from the fluorescent body 40, is reflected by the metal film 67, so that the illumination light can be efficiently used. When the fluorescent body 40 is held in the fluorescent body-holding portion 69, the end faces of the fluorescent body 40 and the metal film 67 are formed so as to be flush with the end face 66a of the ferrule body 66. The insertion hole 68 is formed along the central axis of the ferrule 60. The tip portion of the optical fiber 39A is fitted to the insertion hole 68, and is held on the rear side of the fluorescent body 40.

The first and second sleeve members 61 and 62 are formed in a substantially cylindrical shape so as to have the same outer diameter. When a protrusion 61a formed at the base end of the first sleeve member 61 and a recess 62a formed at the tip of the second sleeve member 62 are fitted to each other, the first and second sleeve members 61 and 62 can be joined to each other so that the outer peripheral surfaces of the first and second sleeve members 61 and 62 continues to each other. Meanwhile, as for the joining of the first and second sleeve members 61 and 62, the dimensions of the protrusion 61a and the recess 62a may be set so that the protrusion 61a and the recess 62a are tightly fitted to each other and the first and second sleeve members 61 and 62 may adhere to each other.

The first sleeve member 61 includes a receiving portion 70, which receives the protective cover 38, and a fitting hole 71, in which an outer peripheral surface 66b of the ferrule body 66 is fitted, in this order from the tip side. The receiving portion 70 is formed so as to have an inner diameter that is larger than the diameter of the fitting hole 71. The receiving portion 70 includes an inner peripheral surface 70a that faces an outer peripheral surface 38a of the protective cover 38 and a bottom face 70b that crosses the inner peripheral surface 70a and faces the base end face of the protective cover 38. The protective cover 38 adheres to the receiving portion 70, so that the tip of the sleeve member 61 is sealed. The fitting hole 71 continues up to the rear end face of the first sleeve member 61 from the bottom face 70b along the axis of the sleeve member 61. The second sleeve member 62 includes a fitting hole 72 of which the inner diameter is larger than the diameter of the fitting hole 71. When the first and second sleeve members 61 and 62 are joined to each other, the ferrule body 66 is received in the fitting holes 71 and 72 and the ferrule 60 does not protrude from the base end of the second sleeve member 62.

The protective cover 38 is made of a material through which illumination light (white light) emitted from the fluorescent body 40, that is, blue laser light that is transmitted through the fluorescent body 40 while being diffused in the fluorescent body 40 and green to yellow fluorescent light that is excited and emitted from the fluorescent body 40 can be transmitted, so as to have a substantially disc shape. The protective cover 38 is made of, for example, silica glass, sapphire glass, or the like.

A step of manufacturing the illumination optical system unit 26A having the above-mentioned structure, particularly, a step of sealing the fluorescent body 40 in the first sleeve member 61 will be described with reference to FIGS. 7A to 7C. First, as shown in FIG. 7A, the protective cover 38 is fitted to the receiving portion 70 and the protective cover 38 and the first sleeve member 61 adhere to each other, so that the first sealing portion 63 for sealing the tip side of the fluorescent body 40 is formed. In a method of applying an adhesive 76 when the protective cover 38 and the first sleeve member 61 adhere to each other, for example, the adhesive 76 is allowed to flow into a gap between the protective cover 38 and the first sleeve member 61 after the protective cover 38 is fitted to the receiving portion 70. Meanwhile, the method is not limited thereto, and the protective cover 38 may be fitted to the receiving portion 70 after the adhesive 76 is applied to the protective cover 38 or the receiving portion 70. For example, a silicon adhesive is used as the adhesive 76.

Next, as shown in FIG. 7B, the ferrule 60, which holds the fluorescent body 40 and the optical fiber 39A, is inserted into the first sleeve member 61 so that the tip of the ferrule 60 comes into contact with the protective cover 38. Further, as shown in FIG. 7C, a magnet 75 is disposed at a position where the magnet 75 comes into contact with the tip of the protective cover 38. Since the metal film 67, which is a magnetic body, is formed in the ferrule 60 as described above, magnetic force is generated between the magnet 75 and the metal film 67, so that attractive magnetic force between the magnet 75 and the metal film 67 is generated. Accordingly, since the ferrule 60 including the metal film 67 is pressed against the protective cover 38 by magnetic force-biasing, the fluorescent body 40 positioned at the tip of the ferrule 60 comes into close contact with the protective cover 38.

Furthermore, while a state of FIG. 7C is maintained, the adhesive 76 is allowed to flow into a gap between the base end portion of the first sleeve member 61 and the ferrule 60 and is solidified so that the second sealing portion 64 is formed (second sealing step). The protrusion 61a of the first sleeve member 61 is fitted to the recess 62a of the second sleeve member 62 and the second sleeve member 62 and the optical fiber 39A are covered with the protective tube 65, so that the illumination optical system unit 26A is completed.

As described above, the metal film 67, which is the magnetic body, is formed on a part of the ferrule 60 and the protective cover 38 and the fluorescent body 40 adheres to each other while coming into close contact with each other by magnet-biasing in the second sealing step, so that the second sealing portion 64 is formed. Accordingly, it is possible to reliably seal the tip side of the fluorescent body 40. Since the first and second sealing portions 63 and 64 sufficiently seal the tip side of the fluorescent body 40, the first and second sealing portions 63 and 64 prevent gas from entering a gap between the fluorescent body 40 and the protective cover 38 when diagnosis using the electronic endoscope 12, washing and disinfection process or the like is performed. Accordingly, it is possible to prevent the degradation of the fluorescent body 40 and the metal film 67. Further, since the fluorescent body 40 and the protective cover 38 are allowed to come into close contact with each other by magnetic force-biasing, it is not necessary to push the optical fiber 39A. Accordingly, it is possible to improve the yield rate of the illumination optical system unit 26A.

In the first embodiment, the protective cover 38 and the fluorescent body 40 have been allowed to come into close contact with each other by magnetic force-biasing using the magnet in the manufacturing step. However, the invention is not limited thereto, and magnetic force may be generated by a component itself of an illumination optical system unit 80 as in a second embodiment shown in FIG. 8. In this case, the illumination optical system unit 80 includes a protective cover 81 of which a part is made of a magnet. Meanwhile, the same members as those of the first embodiment are denoted by the same reference numerals, and the description thereof will be omitted.

The protective cover 81 includes a substantially disc-shaped cover body 82 that is made of sapphire glass or the like and an annular magnet 83 that is disposed along the peripheral edge of a base end side of the cover body 82. The cover body 82 and the magnet 83 are integrated with each other. The magnet 83 is made of, for example, iron, ferrite, or the like, and is formed not to protrude from the outer peripheral surface and the base end face of the cover body 82. For example, the cover body 82 and the magnet 83 of the protective cover 81 are separately formed and are joined to each other by adhesion or the like. Meanwhile, the magnet 83 is provided at a position where the magnet does not prevent blue laser light, which is transmitted through the fluorescent body 40 while being diffused in the fluorescent body 40, and green to yellow fluorescent light, which is excited and emitted from the fluorescent body 40, from being transmitted through the cover body 82 when the illumination optical system unit 80 is completed.

A step of manufacturing the illumination optical system unit 80 having the above-mentioned structure, particularly, a step of sealing the fluorescent body 40 in the first sleeve member 61 will be described with reference to FIGS. 9A to 9C. First, as shown in FIG. 9A, the protective cover 81 is fitted to the receiving portion 70 and the protective cover 81 and the first sleeve member 61 adhere to each other, so that the first sealing portion 63 for sealing the tip side of the fluorescent body 40 is formed. Meanwhile, when the protective cover 81 and the first sleeve member 61 adhere to each other, the adhesive 76 is allowed to flow in as in the case in which the protective cover 38 and the first sleeve member 61 of the first embodiment adhere to each other.

Next, as shown in FIG. 9B, the ferrule 60, which holds the fluorescent body 40 and the optical fiber 39A, is inserted into the first sleeve member 61 so that the tip of the ferrule 60 comes into contact with the protective cover 81. Since the metal film 67, which is a magnetic body, is formed in the ferrule 60, magnetic force is generated between the magnet 83 and the metal film 67, so that attractive magnetic force between the magnet 83 and the metal film 67 is generated. Accordingly, since the ferrule 60 including the metal film 67 is pressed against the protective cover 81 by magnetic force-biasing, the fluorescent body 40 positioned at the tip of the ferrule 60 comes into close contact with the protective cover 81. Further, while a state of FIG. 9B is maintained, the adhesive 76 is allowed to flow into a gap between the base end portion of the first sleeve member 81 and the ferrule 60 and is solidified so that the second sealing portion 64 is formed (second sealing step).

As described above, the metal film 67, which is the magnetic body, is provided on a part of the ferrule 60 and the magnet 83 is provided on a part of the protective cover 81, and the protective cover 38 and the fluorescent body 40 adheres to each other while the protective cover 38 and the fluorescent body 40 come into close contact with each other by magnet-biasing, which occurs between the magnet 83 and the metal film 67, in the second sealing step, so that the second sealing portion 64 is formed. Accordingly, it is possible to reliably seal the tip side of the fluorescent body 40.

Figure 10:
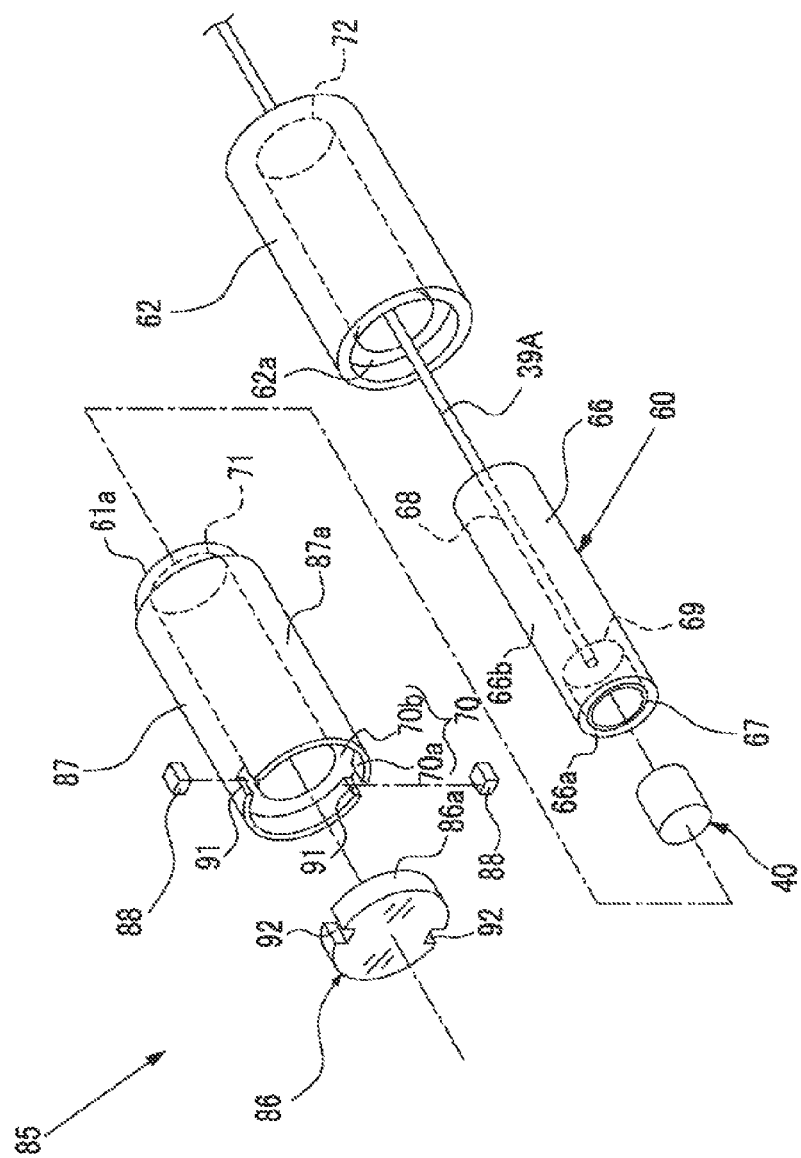
FIG. 10 is an exploded perspective view showing the structure of a modification that uses fitting members fitted to a protective cover.

The protective cover 81 integrated with the magnet 83 has been used as a component of the illumination optical system unit 80 in the second embodiment so that the protective cover 81 is subjected to magnetic force-biasing. However, the invention is not limited thereto, and an illumination optical system unit 85 that is a modification of the second embodiment shown in FIG. 10 includes fixing members 88 (fitting members) that are made of a magnet and are fitted to both a protective cover 86 and a first sleeve member 87. In this case, rectangular cut-out portions 91, which pass through an outer peripheral surface 87a and a receiving portion 70, are formed at the first sleeve member 87, and the protective cover 86 is cut out from an outer peripheral surface 86a in a radial direction so that grooves 92 having the same width as the width of the cut-out portion 91 are formed at the protective cover 86. The fixing members 88 are formed in the shape of a column that has a rectangular cross-section and the same width as the widths of the cut-out portion 91 and the groove 92. Further, the first sleeve member 87 includes a receiving portion 70, a fitting hole 71, and a protrusion 61a that are the same as those of the first sleeve member 61 used in the first and second embodiments.

When the fixing members 88 are fitted to the cut-out portions 91 and the grooves 92 from the outer peripheral surface 87a while the protective cover 86 is fitted into the receiving portion 70 of the first sleeve member 87, the protective cover 86 can be fixed to the sleeve member 87. Meanwhile, the cut-out portions 91 are formed at two positions on the sleeve member 87 and the grooves 92 are formed at two positions on the protective cover 86 in FIG. 10, but are not limited thereto. Each of the cut-out portion 91 and the groove 92 may be formed at one position, and may be formed at three or more positions. Furthermore, the shape of the fixing member 88 is not limited to the shape of a column that has a rectangular cross-section and is to be fitted to the cut-out portion 91 and the groove 92, and may be the shape of a ring that is fitted to the outer peripheral surfaces of the protective cover 86 and the first sleeve member 87.

Figure 11:
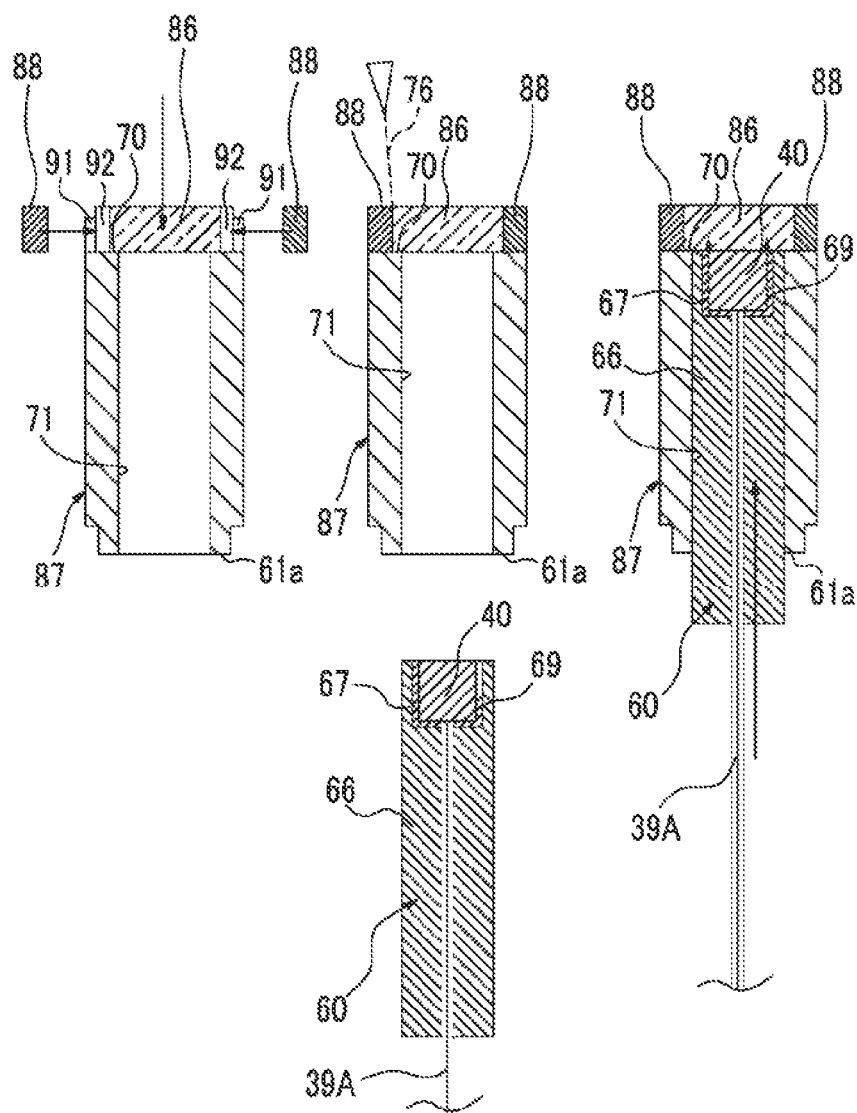
FIGS. 11A to 11C are explanation views illustrating first and second sealing steps of the modification that uses the fitting member fitted to the protective cover.

A step of manufacturing the illumination optical system unit 85 having the above-mentioned structure, particularly, a step of sealing the fluorescent body 40 in the first sleeve member 87 will be described with reference to FIGS. 11A to 11C. First, as shown in FIG. 11A, the protective cover 86 is fitted to the receiving portion 70 and the positions of the grooves 92 are allowed to correspond to the positions of the cut-out portions 91. Further, as shown in 11B, the fixing members 88 are fitted to the cut-out portions 91 and the grooves 92 and the protective cover 86 and the first sleeve member 87 adhere to each other so that a first sealing portion 63 for sealing the tip side of the fluorescent body 40 is formed.

Next, as shown in FIG. 11C, the ferrule 60, which holds the fluorescent body 40 and the optical fiber 39A, is inserted into the first sleeve member 87 so that the tip of the ferrule 60 comes into contact with the protective cover 86. Magnetic force is generated between the fixing members 88 and the metal film 67, so that attractive magnetic force between the fixing members 88 and the metal film 67 is generated. Accordingly, since the ferrule 60 including the metal film 67 is pressed against the protective cover 86 by magnetic force-biasing, the fluorescent body 40 positioned at the tip of the ferrule 60 comes into close contact with the protective cover 86. Further, while a state of FIG. 11C is maintained, the adhesive 76 is allowed to flow into a gap between the base end portion of the first sleeve member 87 and the ferrule 60 and is solidified so that the second sealing portion 64 is formed (second sealing step).

Figure 12:
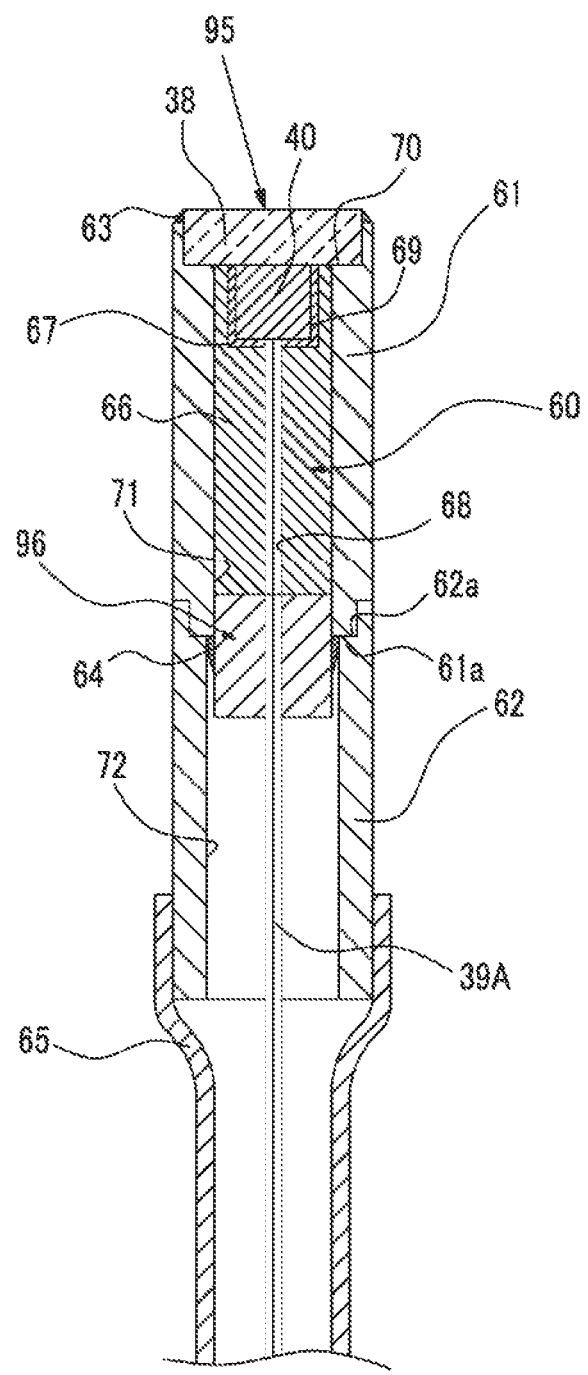
FIG. 12 is a cross-sectional view showing a modification in which a magnet is provided on a base end side of a holding member.

The metal film 67 as a magnetic body, which is provided on a part of the ferrule 60, has been made of magnetic metal in each of the embodiments. However, the invention is not limited thereto, and a cylindrical magnet 96 may be provided at the base end portion of the ferrule body 66 as in an illumination optical system unit 95 shown in FIG. 12. Iron, ferrite, or the like is used as the magnet 96. In this case, the metal film 67 is made of non-magnetic metal, such as aluminum or silver. Further, the ferrule body 66 has been made of a non-magnetic material and a part of the ferrule 60 has been made of a magnetic material in each of the embodiments. However, the invention is not limited thereto, and the ferrule body 66 may be made of a magnet, such as iron or ferrite. In this case, the metal film 67 is made of a non-magnetic metal, such as aluminum or silver.

Furthermore, in the second embodiment, the protective cover and the fluorescent body have been allowed to come into close contact with each other by magnetic force-biasing that is caused by the magnet forming a part of the protective cover or the magnet fitted to the protective cover and the magnetic body provided on a part of the ferrule. However, the invention is not limited thereto, and a magnetic body may be contained in the adhesive, which allows the protective cover and the sleeve member to adhere to each other, so that the protective cover and the fluorescent body are allowed to come into close contact with each other by magnetic force-biasing that is caused by the adhesive and the magnetic body provided on a part of the ferrule 60. Meanwhile, in this case, it is preferable that a part of the ferrule 60 be made of a magnet, such as iron or ferrite.

Further, the electronic endoscope, which observes an image of the state of a subject taken by an imaging element, has been described by way of example in the embodiments. However, the invention is not limited thereto, and also may be applied to an endoscope that observes the state of a subject by an optical image guide. Furthermore, the endoscope including two illumination optical system units has been described by way of example in the embodiments. However, the invention is not limited thereto, and also may be applied to an endoscope including one illumination optical system unit or an endoscope including three or more illumination optical system units.

What is claimed is:
1. An illumination optical system unit for an endoscope comprising:
an optical fiber that guides laser light supplied from a laser light source to a tip thereof and emits the laser light;
a fluorescent body that is excited by the laser light emitted from the optical fiber and emits fluorescent light and forms white light formed of the fluorescent light and the laser light;
a holding member including a fluorescent body-holding portion of which a tip side is opened and which holds the fluorescent body and a through hole which continues to a base end of the fluorescent body-holding portion and into which the optical fiber is inserted, at least a part of the holding member being formed of a magnetic body;
a sleeve member of which a tip and a base end are opened and into which the holding member is fitted, the optical fiber protruding from the base end of the sleeve member;
a protective cover that covers a tip side of the fluorescent body and allows the fluorescent light and the laser light to be transmitted therethrough;

a first sealing portion that is formed by the adhesion between the protective cover and the sleeve member and seals the tip side of the fluorescent body; and a second sealing portion that allows the holding member and the sleeve member to adhere to each other so that a tip of the holding member is allowed to come into close contact with the protective cover by biasing the holding member toward the protective cover by magnetic force after the protective cover and the sleeve member adhered to each other, and seals a base end side of the fluorescent body.

2. The illumination optical system unit for an endoscope according to claim 1,
wherein the second sealing portion is formed so that a magnet is disposed on the protective cover to bias the holding member toward the protective cover by magnetic force.

3. The illumination optical system unit for an endoscope according to claim 1,
wherein a part of the protective cover is made of a magnet, and
the second sealing portion is formed so that the holding member is biased toward the protective cover by magnetic force generated between the protective cover and the holding member.

4. The illumination optical system unit for an endoscope according to claim 1, further comprising:
a fitting member that is fitted to the protective cover and is made of a magnet,
wherein the second sealing portion is farmed so that the holding member is biased toward the protective cover by magnetic force generated between the fitting member and the holding member.

5. The illumination optical system unit for an endoscope according to claim 4,
wherein the fitting member is a fixing member that is fitted to the sleeve member together with the protective cover and fixes the protective cover to the sleeve member.

6. The illumination optical system unit for an endoscope according to claim 1,
wherein, the first sealing portion is made of an adhesive containing a magnetic body, and
the second sealing portion is formed so feat the holding member is biased toward the protective cover by magnetic force generated between the adhesive and the holding member.

7. The illumination optical system unit for an endoscope according to claim 1,
wherein the holding member Includes a body that is formed of a non-magnetic body, and a metal film that is provided on the surface of the fluorescent body-holding portion, is made of magnetic metal, and reflects white light emitted from the fluorescent body.

8. The illumination optical system unit for an endoscope according to claim 2,
wherein the holding member includes a body that is formed of a non-magnetic body, and a metal film that is provided on the surface of the fluorescent body-holding portion, is made of magnetic metal, and reflects white light emitted from the fluorescent body.

9. The illumination optical system unit for an endoscope according to claim 3,
wherein the holding member includes a body that is formed of a non-magnetic body, and a metal film that is provided on the surface of the fluorescent body-holding portion, is made of magnetic metal, and reflects white light emitted from the fluorescent body.

10. The illumination optical system unit for an endoscope according to claim 4,
wherein the holding member includes a body that is formed of a non-magnetic body, and a metal film that is provided on the surface of the fluorescent body-holding portion, is made of magnetic metal, and reflects white light emitted from the fluorescent body.

11. The illumination optical system unit for an endoscope according to claim 1,
wherein the holding member includes a body that is made of a magnet, and a metal film that is provided on the surface of the fluorescent body-holding portion, is made of non-magnetic metal, and reflects white light emitted from the fluorescent body.

12. The illumination optical system unit for an endoscope according to claim 2,
wherein the holding member includes a body that is made of a magnet, and a metal film that is provided on the surface of the fluorescent body-holding portion, is made of non-magnetic metal, and reflects white light emitted from the fluorescent body.

13. The illumination optical system unit for an endoscope according to claim 3,
wherein the holding member includes a body that is made of a magnet, and a metal film that is provided on the surface of the fluorescent body-holding portion, is made of non-magnetic metal, and reflects white light emitted from the fluorescent body.

14. The illumination optical system unit for an endoscope according to claim 4,
wherein the holding member includes a body that is made of a magnet, and a metal film that is provided on the surface of the fluorescent body-holding portion, is made of non-magnetic metal, and reflects white light emitted from the fluorescent body.

15. The illumination optical system unit for an endoscope according to claim 1,
wherein the holding member includes a body that is formed of a non-magnetic body, and a magnet that is provided at a base end side of the body.

16. The illumination optical system unit for an endoscope according to claim 2,
wherein the holding member includes a body that is formed of a non-magnetic body, and a magnet that is provided at a base end side of the body.

17. The illumination optical system unit for an endoscope according to claim 3,
wherein the holding member includes a body that is formed of a non-magnetic body, and a magnet that is provided at a base end side of the body.

18. The illumination optical system unit for an endoscope according to claim 4,
wherein the holding member includes a body that is formed of a non-magnetic body, and a magnet that is provided at a base end side of the body.

19. A method of manufacturing an illumination optical system unit for an endoscope according to claim 1, the method comprising:
a first sealing step of sealing the tip side of the fluorescent body by allowing the sleeve member and the protective cover to adhere to each other; and
a second sealing step of sealing a base end side of the fluorescent body by allowing the sleeve member and the holding member to adhere to each other so that a tip of the holding member is allowed to come into close contact with the protective cover by inserting the holding member into the sleeve member, allowing the optical fiber to protrude from base ends of the holding member and the sleeve member, and biasing the holding member toward the protective cover by magnetic force after the sleeve member and the protective cover adhered to each other.

* * * * *